US011891606B2

(12) United States Patent
Tachas

(10) Patent No.: US 11,891,606 B2
(45) Date of Patent: Feb. 6, 2024

(54) METHODS FOR TREATING MULTIPLE SCLEROSIS USING ANTISENSE OLIGONUCLEOTIDES

(71) Applicant: Antisense Therapeutics Ltd, Victoria (AU)

(72) Inventor: George Tachas, Victoria (AU)

(73) Assignee: Antisense Therapeutics Ltd, Victoria (AU)

(*) Notice: Subject to any disclaimer, the term of this patent is extended or adjusted under 35 U.S.C. 154(b) by 417 days.

(21) Appl. No.: 16/622,820

(22) PCT Filed: Jun. 15, 2018

(86) PCT No.: PCT/AU2018/050598
§ 371 (c)(1),
(2) Date: Dec. 13, 2019

(87) PCT Pub. No.: WO2018/227254
PCT Pub. Date: Dec. 20, 2018

(65) Prior Publication Data
US 2021/0147851 A1 May 20, 2021

(30) Foreign Application Priority Data
Jun. 16, 2017 (AU) .................................. 2017902314

(51) Int. Cl.
| | | |
|---|---|---|
| *C12N 15/113* | (2010.01) | |
| *A61P 25/28* | (2006.01) | |
| *A61K 31/437* | (2006.01) | |
| *A61K 31/7125* | (2006.01) | |
| *A61K 38/07* | (2006.01) | |
| *A61K 38/21* | (2006.01) | |
| *C12Q 1/68* | (2018.01) | |

(52) U.S. Cl.
CPC ........ *C12N 15/1138* (2013.01); *A61K 31/437* (2013.01); *A61K 31/7125* (2013.01); *A61K 38/07* (2013.01); *A61K 38/215* (2013.01); *A61P 25/28* (2018.01); *C12N 2310/11* (2013.01); *C12N 2310/315* (2013.01); *C12N 2310/3341* (2013.01); *C12N 2310/346* (2013.01); *C12N 2320/31* (2013.01); *C12N 2320/32* (2013.01); *C12N 2320/35* (2013.01)

(58) Field of Classification Search
None
See application file for complete search history.

(56) References Cited

U.S. PATENT DOCUMENTS

| | | | | |
|---|---|---|---|---|
| 8,415,314 | B2* | 4/2013 | Klinger | ................... A61P 25/00 536/24.5 |
| 8,759,314 | B2* | 6/2014 | Klinger | .............. C12N 15/1138 536/24.5 |
| 2010/0119480 | A1* | 5/2010 | Klinger | ................... A61P 25/00 424/133.1 |
| 2013/0345293 | A1* | 12/2013 | Klinger | ................... A61P 25/00 514/44 R |

FOREIGN PATENT DOCUMENTS

WO    WO 2012/034194 A1    3/2012

OTHER PUBLICATIONS

Alter et al., "Determinants of human B-cell migration across brain endothelial cells". J Immunol. May 1, 2003;170(9): 4497-4505.
Anzctr, Australian New Zealand Clinical Trials Registry, Registration CTRN12608000226303—Trial registered on, (As updated on Jul. 21, 2009), available online:, URL:https://www.anzctr.org.au/Trial/Registration/TrialReview.aspx?id=82556&showHistory=true &isReview=true, 9 pages.
Barkhof et al., "Ibudilast in relapsing-remitting multiple sclerosis: a neuroprotectant?" Neurology 2010;74;1033-1040.
Bastianello et al., "Changes in magnetic resonance imaging disease measures over 3 years in mildly disabled patients with relapsing-remitting multiple sclerosis receiving interferon β-1a in the COGnitive Impairment in Multiple Sclerosis (COGIMUS) study", BMC Neurol. Dec. 2011;11(1): 1-9.
Coles et al., "Alemtuzumab for patients with relapsing multiple sclerosis after disease-modifying therapy: a randomised controlled phase 3 trial". The Lancet. Nov. 24, 2012;380(9856): 1819-1828.
Brex et al., "The effect of IFNβ-1b on the evolution of enhancing lesions in secondary progressive MS", Neurology Dec. 26, 2001;57(12): 2185-2190.
Brex et al., "A longitudinal study of abnormalities on MRI and disability from multiple sclerosis", N Engl J Med. Jan. 17, 2002, 346(3): 158-164.
Carrasco et al., "B-cell activation by membrane-bound antigens is facilitated by the interaction of VLA-4 with VCAM-1". EMBO Feb. 22, 2006;25(4):889-99.
Frohman et al., "The utility of MRI in suspected MS: Report of the Therapeutics and Technology Assessment Subcommittee of the American Academy of Neurology", Neurology Sep. 9, 2003;61(5): 602-611.
Havla et al., "Interdisciplinary Risk Management in the Treatment of Multiple Sclerosis". Dtsch Arztebl Int. Dec. 2016;113(51-52): 879-886.
Hauser et al., "Ocrelizumab versus Interferon Beta-1a in Relapsing Multiple Sclerosis". N Engl J Med. 2017; 376 (3): 221-234.

(Continued)

*Primary Examiner* — Sean McGarry
(74) *Attorney, Agent, or Firm* — Knobbe, Martens, Olson & Bear, LLP

(57) ABSTRACT

A method for treating a patient suffering from multiple sclerosis, including progressive forms of multiple sclerosis, comprising periodically administering a pharmaceutical composition comprising a therapeutically effective amount of OLIGONUCLEOTIDE I to the patient, thereby treating the patient.

21 Claims, No Drawings

Specification includes a Sequence Listing.

(56) References Cited

OTHER PUBLICATIONS

Jen et al., Suppression of Gene Expression by Targeted Disruption of Messenger RNA: Available options and current strategies. Stem cells. Sep. 2000;18(5): 307-319.

Kappos et al., "Efficacy and safety of siponimod in secondary progressive MS: Results of the placebo controlled, double-blind, Phase III EXPAND study" In *Multiple Sclerosis Journal* Sep. 1, 2016 (vol. 22, pp. 828-829). 1 Olivers Yard, 55 City Road, London EC1Y 1SP, England: Sage Publications Ltd.; ECTRIMS 2016; Abstract 250.

Kappos et al "Siponimod versus placebo in secondary progressive multiple sclerosis (EXPAND): a double-blind, randomised, phase 3 study". The Lancet, Mar. 31, 2018;391(10127): 1263-1273.

Limmroth et al., "Prediction of Optimal dosing regimen for TV-1102, a novel anti VLA-4 antisense drug". Multiple Sclerosis (Sep. 2009), vol. 15 No 9, Supp. Suppl S, pp. S125, abstract No. P435.

Limmroth et al., "CD49d antisense drug ATL1102 reduces disease activity in patients with relapsing-remitting MS", Neurology Nov. 11, 2014;83(20): 1780-1788 with Correction Addendum.

Lo et al., "Integrin-dependence of lymphocyte entry into the splenic white pulp". J Exp Med. Feb. 3, 2003;197(3): 353-361.

Montalban et al., "Ocrelizumab versus placebo in primary progressive multiple sclerosis". New Engl J Med. Jan. 19;376(3): 209-220.

Niino et al., "Natalizumab effects on immune cell responses in multiple sclerosis". Ann. Neurol. May 2006;59(5): 748-754.

Plavina et al., "Anti-JC virus antibody levels in serum or plasma further define risk of natalizumab-associated progressive multifocal leukoencephalopathy". Ann Neurol. Dec. 2014;76(6): 802-812.

Polman et al., "AFFIRM Investigators A randomized, placebo-controlled trial of natalizumab for relapsing multiple sclerosis". N Engl J Med. Mar. 2, 2006;354(9): 899-910.

Rovira et al., "MR in the diagnosis and monitoring of multiple sclerosis: An overview", Eur J Radiol. Sep. 1, 2008;67(3): 409-414.

Stankiewicz et al., "Role of immunosuppressive therapy for the treatment of multiple sclerosis" Neurotherapeutics Jan. 2013;10(1): 77-88.

Steinman L., "Blocking adhesion molecules as therapy for multiple sclerosis: Natalizumab", Nature Rev Drug Disc. Jun. 2005;4(6): 510-518.

Tchilian et al., "Anti-α4 integrin antibody induces apoptosis in murine thymocytes and staphylococcal enterotoxin B-activated lymph node T-cells". Immunology Nov. 1997;92(3):321-7.

Van Oosten et al., "Treatment of multiple sclerosis with the monoclonal anti-CD4 antibody cM-T412: Results of a randomised, double-blind, placebo-controlled MR-monitored phase II trial.", Neurology. Neurology. Aug. 1, 1997;49(2):351-7.

Zivadinov et al., "Effect of glatiramer acetate three-times weekly on the evolution of new, active, multiple sclerosis lesions into T1-hypintense "black holes": A post hoc magnetic resonance imaging analysis", J Neurol. Mar. 2015;262(3): 648-653.

\* cited by examiner

SEQUENCE LISTING

```
<160> NUMBER OF SEQ ID NOS: 1

<210> SEQ ID NO 1
<211> LENGTH: 20
<212> TYPE: DNA
<213> ORGANISM: artificial
<220> FEATURE:
<223> OTHER INFORMATION: Chemically synthesized
<220> FEATURE:
<221> NAME/KEY: 2'-O-(2-methoxyethyl) 5-methylcytosine
<222> LOCATION: (1)..(1)
<220> FEATURE:
<221> NAME/KEY: 2'-O-(2-methoxyethyl) modified ribonucleosides
<222> LOCATION: (1)..(3)
<220> FEATURE:
<221> NAME/KEY: 2'-O-(2-methoxyethyl) 5-methyluracil
<222> LOCATION: (2)..(2)
<220> FEATURE:
<221> NAME/KEY: 2'-deoxyribonucleosides
<222> LOCATION: (4)..(12)
<220> FEATURE:
<221> NAME/KEY: 2'-deoyxy 5-methylcytosine
<222> LOCATION: (7)..(7)
<220> FEATURE:
<221> NAME/KEY: 2'-O-(2-methoxyethyl) modified ribonucleosides
<222> LOCATION: (13)..(20)
<220> FEATURE:
<221> NAME/KEY: 2'-O-(2-methoxyethyl) 5-methyluracil
<222> LOCATION: (13)..(13)
<220> FEATURE:
<221> NAME/KEY: 2'-O-(2-methoxyethyl) 5-methylcytosine
<222> LOCATION: (14)..(15)
<220> FEATURE:
<221> NAME/KEY: 2'-O-(2-methoxyethyl) 5-methyluracil
<222> LOCATION: (17)..(18)
<220> FEATURE:
<221> NAME/KEY: 2'-O-(2-methoxyethyl) 5-methycytosine
<222> LOCATION: (19)..(19)
<220> FEATURE:
<221> NAME/KEY: 2'-O-(2-methoxyethyl) 5-methyuracil
<222> LOCATION: (20)..(20)

<400> SEQUENCE: 1
cugagtctgt ttuccauucu                                            20
```

METHODS FOR TREATING MULTIPLE SCLEROSIS USING ANTISENSE OLIGONUCLEOTIDES

CROSS-REFERENCE TO RELATED APPLICATIONS

This application is a U.S. National Phase under 35 U.S.C. § 371 of International Application No. PCT/AU2018/050598, filed Jun. 15, 2018, which claims priority to Australian Patent Application No. 2017902314, filed Jun. 16, 2017, each of which is hereby incorporated by reference in its entirety.

Throughout this application various publications are referenced by Arabic numeral in parentheses. The full citation of the corresponding reference appears at the end of the specifications before the claims. The disclosures of these publications in their entireties are hereby incorporated by reference into this application in order to more fully describe the state of the art to which this invention pertains.

FIELD AND BACKGROUND OF THE INVENTION

The present invention relates to methods of treating Multiple Sclerosis, including progressive forms of Multiple Sclerosis.

Multiple Sclerosis

Multiple Sclerosis (MS) is a common neurological disease affecting more than 1 million people worldwide. Its prevalence rate varies between races and geographical latitude, ranging from more than 100 per 100,000 in Northern and Central Europe to 50 per 100,000 in Southern Europe. MS affects approximately 400,000 people in the United States. MS is the most common cause of neurological disability in young and middle-aged adults. Typically, the disease becomes evident before the age of 30 in about 50% of patients; in 25% of the patients the onset of disease is between the ages of 30 to 40, and in 25% the disease appears between the ages of 40 to 50. The female to male ratio is 2:1 (Alonso and Mernan, 2008).

MS and the resulting neurological damage have a major physical, psychological, social and financial impact on the patients and on their families. The most common clinical symptoms of MS are paresis, paraesthesia, visual impairment, sexual, bowel, and urinary dysfunction, spasticity, and incoordination. 40 to 50% of patients suffer from cognitive dysfunctions. The extent of neurological deficit, the rate of progression and the frequency of relapse are highly variable among the affected individuals (Committee notes for Proprietary Medicinal Products, 1997 and 1999).

Most MS patients have a normal life span marked by numerous years of severe progressive disability. The causes of death in patients with MS are respiratory or urinary tract infections rather than the disease itself. There are several distinct types of MS: relapsing-remitting multiple sclerosis (RRMS), which is characterized by unpredictable acute episodes of neurological dysfunction (relapses), followed by variable recovery and periods of clinical stability. 80% to 85% of MS patients are diagnosed with RRMS. More than 50% of the patients having RRMS develop sustained deterioration with or without relapses superimposed; this form is called secondary progressive MS (SPMS). Some MS patients developing a progressive deterioration from the beginning can also develop relapses later on; this uncommon form is called primary progressive-relapsing multiple sclerosis (Committee notes for Proprietary Medicinal Products, 1997 and 1999).

Approximately 15% of overall MS patients develop a sustained deterioration of their neurological function from the beginning. This form is known as primary progressive MS or PPMS. The diagnosis is currently according to the McDonald's criteria (McDonald, 2001). The outcome of a diagnostic evaluation is either "Multiple Sclerosis", "possible MS" (for those at risk for MS, but for whom diagnostic evaluation is equivocal), or "not MS" (McDonald, 2001). Finally, the term clinically isolated syndrome (CIS) applies to those patients who have suffered a first clinical attack but do not meet the classical diagnostic criteria for definite MS. Currently, the presence of new lesions in a second MRI performed at least three months apart is an accepted criterion for a diagnosis of MS in these patients. 10% to 20% of patients with an isolated syndrome will not develop MS.

MS is an inflammatory disease that damages myelin in the Central Nervous System (CNS) causing neurological impairment and, frequently, severe disability. The etiology of MS remains mostly unknown. It is generally assumed that MS is triggered by a combination of autoimmunity, infection and genetic predisposition (Committee notes for Proprietary Medicinal Products, 1997 and 1999). Autoimmune response against myelin components proceeding through the activation of CD4+ T lymphocytes, loss of proper regulation on Th1/Th2 lymphocytes, production of anti-myelin antibodies by B lymphocytes, and possibly, inhibition of CD8+ cytotoxic/suppressor T lymphocytes underlie the pathogenesis of the MS.

MS is characterized by scattered regions of inflammation within the white substance of the CNS, brain and spinal cord. Focal inflammatory events eventually lead to demyelination of the axonal sheaths, degradation of nerve tissue, and finally, to irreversible neurological damage. Although the exact mechanism by which the MS process is initiated remains largely unknown, the target antigens of the autoimmune response in MS are believed to be part of the CNS myelin.

It is unclear whether the different courses of multiple sclerosis described are due to the same or to distinct pathophysiologic processes. Relapses are considered the clinical expression of acute inflammatory focal lesions whereas progression is considered to reflect the occurrence of demyelination, axonal loss and gliosis. Relapsing remitting multiple sclerosis and secondary progressive multiple sclerosis are probably different stages of the same disease while primary progressive multiple sclerosis may imply different processes.

Myelin basic protein (MBP) and proteolipid protein (PLP) are the most common myelin components. Additional, less abundant constituents of myelin, such as myelin associated glycoproteins (MAG), myelin oligodendrocyte glycoproteins (MOG), and α-β crystalline are also known. There is a considerable ongoing debate regarding the true nature of the target antigen(s) in multiple sclerosis. In general, it appears that involvement of different antigens leads to certain differences in the courses of the disease (Johnson et al., 1986; Chou et al., 1992; de Rosbo et al., 1993; de Rosbo and Ben-Nun, 1998; van Noort et al., 1995; Pelfrey et al., 1996; Diaz-Villoslada et al., 1999; Pender et al., 2000).

MRI-Based Multiple Sclerosis Diagnostic Criteria

All the diagnostic criteria for establishing the diagnosis of MS proposed in the last 50 years are based on three main principles: (1) demonstration of demyelinating lesions disseminated in space (DIS); (2) demonstration of demyelinating lesions disseminated in time (DIT); and (3) reasonable exclusion of alternative explanations for the clinical presentation (Rovira and Leo, 2008).

Conventional MRI

Conventional MRI techniques (cMRI), such as T2-weighted sequences and gadolinium-enhanced T1-weighted sequences (GdT1), are highly sensitive for detecting MS plaques and can provide quantitative assessment of inflammatory activity and lesion load.

MRI studies in patients with Relapsing Remitting Multiple Sclerosis (RRMS) and Secondary progressing Multiple Sclerosis (SPMS), using gadolinium diethylenetriamine pentaacetic acid (Gd-DTPA) as a contrast agent, indicating blood-brain barrier disruption, have revealed that disease activity (defined as the presence of Gd-enhancing lesions on T1-weighted MM) is 5 to 10 times more frequent than is apparent from clinical criteria alone (Van Oosten et al., 1997).

Non-Conventional MRI

Unenhanced T1-weighted imaging, measures of central nervous system atrophy, magnetization transfer imaging, proton magnetic resonance spectroscopy, diffusion-weighted imaging, and functional magnetic resonance imaging, provide a better approximation of the pathological substrate of the multiple sclerosis plaques, have increased the understanding of the pathogenesis of the disease, and have proven useful for studying the natural history of multiple sclerosis and monitoring the effects of new treatments (Rovira and Leo, 2008).

Current Therapeutic Approaches

There is no known cure for MS. The goal of current therapy for relapsing forms of MS (R-MS) including RRMS and secondary progressing multiple sclerosis with superimposed relapses (R-SPMS), is to reduce and prevent GdT1 and new-enlarging T2 brain lesions, relapses and the associated worsening disability progression and to silence the disease. To achieve this, clinicians often switch between several disease modifying immunomodulatory or immunosuppressive drug treatments for each patient, seeking a satisfactory treatment regimen with no evidence of disease activity (NEDA).

Another goal of R-MS therapy is to improve recovery from acute relapse attacks, Steroids are the principal medication for the short-term treatment of acute relapses. The i.v. corticosteroids (e.g. methylprednisolone) can reduce the duration and severity of acute attacks but do not have an effect on the occurrence of new relapses or affect the progression of MS.

Disease modifying immunomodulatory and immunosuppressive drugs are assessed on their ability to reduce or prevent GdT1 and new-enlarging T2 brain lesions, lessen or prevent the number of relapses and their severity, and to reduce or stop disease progression, with no evidence of disease activity (NEDA) on these 3 parameters assessed at NEDA-3. MRI brain lesion reductions are associated with reductions in relapse rate and worsening disease progression clinical parameters in longer-term studies.

For long-term disease management, the US Food and Drug Administration (FDA) have approved several disease modifying drugs for patients with MS. These include interferon beta-1a (Avonex®, Rebif®, and recently Plegridy®), interferon beta-1b (Betaseron®) and glatiramer acetate (Copaxone®) for R-MS. The beta-interferons and Copaxone® are historically the first choice treatment in RRMS patients and have been shown to reduce relapse rates by about $\frac{1}{3}^{rd}$ compared to placebo.

More recently approved oral R-MS disease-modifying therapeutics are Teriflunomide (Aubagio®), an anti-proliferative drug that reduces relapse rates by a $\frac{1}{3}^{rd}$; Dimethyl fumarate (Tecfidera®), an immunoregulatory drug and Fingolimod (Gilenya™) affecting lymphocyte trafficking which reduce relapse rates by about a half in R-MS patient registration studies. Daclizumab (Zinbytra®) a monoclonal antibody inhibitor to the IL-2 receptor alpha subunit on all T-cells is another immmunoregulatory drug and similarly active in R-MS.

Of the more highly active approved monoclonal antibody drugs for R-MS there is the cytolytic antibodies alemtuzumab (Lemtrada®) which ablates CD52+ B and T-cells and ocrelizumab (Ocrevus™) which ablates CD20+ B-cells. Natalizumab (Tysabri®) the first antibody drug registered by the FDA and EMA in R-MS targets adhesion molecule protein very late antigen (VLA-4) and is a pan VLA-4 antagonist blocking all VLA-4 on T and B cells and VLA-4 positive leukocyte trafficking.

Natalizumab is potentially the most effective drug in RRMS when comparing the NEDA-3 in the treated vs comparator arms in Phase III trials. No evidence of disease activity (no new GdT1 or new-enlarging T2 lesions, no relapses and no confirmed EDSS worsening) observed in Phase III studies was 32%, 48%, and 37% for alemtuzumab, ocrelizumab, and natalizumab, compared to comparator arm 13%, 25%, and 7% respectively (Polman et al., 2006; Coles et al., 2012; Hauser et al., 2017). Natalizumab has been shown to reduce relapse rates by two thirds and to delay disease progression by 40% but causes progressive mutlifocal leukoencephaolpaghy (PML), a rare and frequently fatal, demyelinating disease of the CNS in a significant number of patients (Plavina et al., 2014). This has led to the drug's restricted indication and/or use in the US and Europe. Alemtuzumab has an increased risk of autoimmune disease with 35% of patients treated with alemtuzumab developing autoimmune thyroid disease within two years and the drug is a third line therapy in the US (Havla et al., 2016). Ocrelizumab has an increased risk in cancer rate including breast cancer, which incidence is to be better determined with longer term use (Montalban et al., 2017).

Another drug, Mitoxantrone (Novantrone®) an antiproliferative cytotoxic agent, first approved in 2000 is registered for use in worsening RRMS, secondary (chronic) progressive MS, progressive relapsing MS but can only be used for two to three years because of safety limitations and is rarely used in the US (Stankiewicz et al., 2013). MS is a heterogeneous immune disease and even with the highly active drug natalizumab, only 37% of RRMS patients achieved NEDA-3, without new GdT1/new enlarging T2 MRI brain lesions, relapses and EDSS disease progression over 2 years (Polman et al., 2006). Natalizumab also reduces MRI brain lesions and relapses in advanced SPMS but is not effective in reducing disease progression not associated with relapses as measured by EDSS. Siponimod, a sphingosine-1-phosphate receptor agonist (like fingolimod), shows a modest level of activity in reducing disease progression in SPMS and registration is being sought (Kappos et al., 2016). Ocrelizumab has recently been registered by the FDA as the first drug to treat PPMS.

MRI Based Response or Non-Response to Treatment

Of the new GdT1 lesions that develop in MS, about 80% will become a white scar T2 lesion, and about one in four T2 lesions convert into a persistent hypointense T1-weighted lesion, known as a "black hole" in un-enhanced T1-weighted imaging scan (Barkhof et al., 2010). A black hole (BH)

represents an area of axonal loss and permanent tissue damage and conversion to BH has been associated with disability progression.

Ibudilast, a phosphodiesterase inhibitor, shows no beneficial effect on the rate of newly active lesions (new GdT1 or new-enlarging T2) forming over 12 months, and relapses. Ibudilast however, reduces the proportion of active lesions at 2 months that evolve into persistent BH at 10 months to 14% and 17% at 60 mg/day and 30 mg/day doses, respectively, compared to 24% in the placebo arm, and thereby slows percentage brain volume change (PBVC), a measure of atrophy, over 12 months. Fewer patients have confirmed disease progression as measured by EDSS over 2 years compared to placebo (Barkhof et al., 2010). Ibudilast is in late stage registration trials for the treatment of MS, including progressive MS, indicating the importance of reducing the evolution of active lesions into BH.

Betaferon (IFNbeta-1b) registered in Europe for use in R-SPMS, reduces the number of new GdT1 lesions, but when new GdT1 lesions do become established, does not alter their course (Brex et al., 2001). Rebif (IFN beta-1a) in RRMS patients reduces BH volume over 3 years at a high 44 µg dose but not at the standard 22 µg dose (Bastianello et al., 2011). A high 40 mg dose (twice the standard 20 mg dose) of copaxone over 12 months is also found to reduce the number of BH (Zivadinov et al., 2015). In a 1292 patient study, copaxone 40 mg dose reduces the proportion of new lesions at 6 months converting to BH at 12 months to 15.8% vs 19.6% for placebo; i.e., an extra 3.8%. Most patients on these three treatments, do not have sufficient reduction in the number of new active lesions, and with only a small reduction of $\frac{1}{3}^{rd}$ in relapses, often switch therapy. Thus, the benefits of these drugs on conversion to (new) active lesions to BH is slow, small, and useful for only the small proportion who don't have breakthrough disease and stay on treatment.

There are a number of unresolved issues with MS drugs, including capacity to treat MS patients with breakthrough disease, who have new active lesions, relapses and progression, and otherwise non-stable disease or who do not tolerate treatment. There is a particular need for drugs to significantly reduce (new) active lesions, and when these (new) active lesions become established, to alter their course and reduce progression to BH to reduce brain atrophy. Consequently there are a number of new therapies under development.

Antisense Theory

Antisense oligonucleotides (AS-ONs) are short stretches of nucleotides or nucleotide derivatives that are complementary to a region of targeted RNA and can specifically suppress expression and other aspects such as processing of that particular transcript. The exact mechanism(s) of AS-ON action is known to be different depending on the type of AS-ONs. Generally, these molecules block gene expression by hybridizing to the target mRNA, resulting in subsequent double-helix formation. This process can occur at any point such as transcription, initiation of translation, or during translation. Some of the possible mechanisms are disruption of splicing, impaired mRNA transport, disruption of translation of the transcripts as well as decreased stability of the mRNA transcript. In the case of many antisense oligodeoxyribonucleotides (AS-ODNs), cellular RNase H is able to bind to the DNA-RNA duplex and hydrolyze the RNA, resulting in reduced transcript numbers and decreased production of protein. Modifications to the deoxy moiety at the 2'-sugar position usually prohibits RNase H recruitment and action in that region of an AS-ODN (Kuang-Yu et al., 2000).

Modified AS-ONs or AS-ON analogs are often employed for in vivo antisense applications due to their increased stability and nuclease resistance. A longer serum half-life ensures that the AS-ON has ample time to reach and interact with its target RNA in the tissue. AS-ODNs with phosphorothioate backbones are widely used due to their longer serum half-life and the fact that they are a suitable RNase H substrate. However, phosphorothioates display high affinity for various cellular proteins, which can result in sequence-nonspecific effects. Many AS-ONs with 2'-modifications of the sugar with groups such as O-methyl, fluoro, O-propyl, 0-allyl, or many others exhibit greater duplex stability with their target mRNA and greater specificity but antisense effects in that 2' modified region are usually independent of RNase H. These modifications create bulk at the 2' position, causing steric hindrance to play a significant role in increasing nuclease resistance. Nucleotide analogs, such as peptide nucleic acids, generally are also nuclease-resistant and often demonstrate superior hybridization properties due to modified backbone charge, although they usually are not acceptable substrates for RNase H (Kuang-Yu et al., 2000).

The traditional goal of the antisense approach to therapeutics is to decrease the level of key proteins in the disease pathogenesis. The use of antisense oligonucleotides as therapeutics has the potential advantage of much greater specificity compared to conventional small molecule drugs. The majority of drugs currently in use modulate the activity of specific proteins by either binding directly to the protein of interest or by binding to other proteins, such as cell surface receptors, which then modulate the target protein. Due to the large number of related proteins, activity classes and protein families performing the same or very similar function, small molecule drugs often bind to, and affect the activity of, more than one target protein. In contrast, the effectiveness of AS-ONs relies on highly specific base-pairing between the oligonucleotide and the target RNA. Therefore, antisense technology enables targeting of a single member of a closely-related protein family and designing therapeutic agents displaying fewer non-specific toxic effects than other, less selective, agents (Helene and Toulme, 1990; Cohen, 1991; Calabretta, 1991; Crooke, 1993; Crooke, 1992).

VLA-4 Integrin

Integrins are heterodimeric adhesion molecules that play key roles in leukocyte maturation, survival, activation, trafficking, and signalling. The VLA-4 integrin consists of α4 chain non-covalently linked to the beta 1 subunit. It is expressed on most leukocytes, whether they occur in peripheral blood, lymphoid tissue, or at sites of inflammation in various organs. VLA-4 is a receptor on the surface of most leukocytes, including most T, B and natural killer (NK) lymphocytes, monocytes, eosinophils, basophils and certain neutrophils in humans (Hemler, 1987). α4 1 binds to VCAM-1 on the activated endothelium and to the C S1 segment of fibronectin found in extracellular matrix. These interactions are critical for leukocyte migration across endothelium and into inflamed tissues. Ligand binding by α4 integrins has diverse biological consequences. VLA-4 plays a role in adhesion of leukocytes to the extracellular matrix (ECM) components fibronectin and osteopontin, to endothelial cell VCAM enabling cell transmigration, and has a role in the maturation, survival, and activation of immune cells (Tchilian et al., 1997; Lo et al., 2003; Alter et al., 2003, Niino et al., 2006; Carrasco and Batista, 2006). The best-known role for α4 is its function as an adhesion molecule guiding leukocytes across vascular endothelium and into sites of inflammation. Leukocytes are recruited from the blood and into tissues by a multi-step process that involves an initial transient rolling of cells along the vascular endothelium followed by firm adhesion and subsequent trans-endothelial migration.

The α4 integrin is unique among adhesion molecules in that it can support both the rolling and firm adhesion steps (Steinman, 2005).

SUMMARY OF THE INVENTION

The inventors have surprising found that ATL1102 treatment reduces conversion of active multiple sclerosis lesions into persistent black holes, a marker of axonal loss and permanent tissue damage, demonstrating a neureoprotective role of ATL1102 in addition to reducing the number of new inflammatory brain lesions.

Accordingly, the invention provides a method for treating a human subject afflicted with a form of multiple sclerosis (MS) characterized by the presence of active lesions detectable by MRI, the method comprising periodically administering to the human subject a pharmaceutical composition comprising a pharmaceutically acceptable carrier and an oligonucleotide having the structure 5'-$^{Me}C^{Me}$UG AGT $^{Me}$CTG TTT $^{Me}U^{Me}C^{Me}$C $A^{Me}U^{Me}U$ $^{Me}C^{Me}$U-3' (SEQ ID NO. 1)

wherein
  each of the 19 internucleotide linkages of the oligonucleotide is an 0,O-linked phosphorothioate diester;
  the nucleotides at the positions 1 to 3 from the 5' end are 2'-O-(2-methoxyethyl) modified ribonucleosides;
  the nucleotides at the positions 4 to 12 from the 5' end are 2'-deoxyribonucleosides;
  the nucleotides at the positions 13 to 20 from the 5' end are 2'-O-(2-methoxyethyl) modified ribonucleosides; and
  all cytosines are 5-methylcytosines ($M^eC$),
or a pharmaceutically acceptable salt of the oligonucleotide, whereby the administration of the pharmaceutical composition is effective to inhibit the conversion of active brain lesions in the subject into hypointense T1-weighted lesions.

In some embodiments, the oligonucleotide is in the form of a stereoisomer.

In some embodiments, the administration inhibits an increase in the number and/or volume of hypointense T1-weighted lesions in the human subject. In other embodiments, the administration inhibits an increase in the number and/or volume of hypointense T1-weighted lesions in the human subject. In some embodiments, the administration inhibits one or more of percentage brain volume change (PBVC), atrophy, or progression of disability in the human subject.

In some embodiments, the proportion of active brain lesions converted into hypointense T1-weighted lesions detectable by MRI after treatment is at least 10% lower, at least 11% lower, at least 12% lower, at least 13% lower, at least 14% lower, at least 15% lower, at least 16% lower, at least 17% lower, at least 18% lower, at least 19%, lower, at least 20% lower, at least 25% lower, at least 30% lower, at least 35% lower, at least 40% lower, at least 45% lower, or at least 50% lower than the proportion of active brain lesions converted into hypointense T1-weighted lesions detectable by MRI in a human subject afflicted with the same form of MS, but not treated with the pharmaceutical composition. In some embodiments, the proportion of active brain lesions converted into hypointense T1-weighted lesions detectable by MRI is about 10%, about 11%, about 12%, about 13%, about 14%, about 15%, about 16%, about 17%, about 18%, about 19%, about 20% after 8 weeks of treatment with the pharmaceutical composition. In another embodiment, the number of active brain lesions converted into hypointense T1-weighted lesions detectable by MRI is less than about 20%, less than about 15%, less than about 14%, less than about 13%, less than about 12%, less than about 11%, or less than about 10%.

In other embodiments, the number of active brain lesions detectable by MRI is reduced by 35%-90% relative to the number in a human subject afflicted with the same form of MS, but not treated with the pharmaceutical composition. In one embodiment, the proportion of active brain lesions converted into hypointense T1-weighted lesions detectable by MRI after treatment is at least 10% lower than the proportion of active brain lesions converted into hypointense T1-weighted lesions detectable by MRI in a human subject afflicted with the same form of MS, but not treated with the pharmaceutical composition, and the number of active brain lesions detectable by MRI is reduced by at least about 35% relative to the number in the human subject afflicted with the same form of MS, but not treated with the pharmaceutical composition.

In further embodiments, the periodic administration of the pharmaceutical composition is once, twice, or three times per week. In other embodiments the periodic administration occurs once per week, once every two weeks, once every three weeks, once every four weeks, once per month, or once per two months. In some embodiments, the periodic administration occurs twice per week.

In some embodiments, the pharmaceutical composition to be administered comprises 200, 400, 600, 800, 1000, 1200, 1400, or 1600 mg of the oligonucleotide. In other embodiments, the pharmaceutical composition comprises 25-400 mg of the oligonucleotide.

In some embodiments, where the periodic administration is to be administered once per week, the pharmaceutical composition comprises 200 mg of the oligonucleotide. In some embodiments, the pharmaceutical composition comprises 100 mg of the oligonucleotide. In one embodiment, the pharmaceutical composition comprises about 70 mg of the oligonucleotide. In another embodiment, the pharmaceutical composition comprises about 50 mg of the oligonucleotide. In another embodiment, the pharmaceutical composition comprises about 25 mg of the oligonucleotide. In another embodiment, the pharmaceutical composition comprises 300 mg of the oligonucleotide.

In other embodiments, where the periodic administration is twice per week, the pharmaceutical composition comprises about 200 mg, about 150 mg, about 100 mg, about 50 mg, about 35 mg, about 25 mg, or about 12.5 mg of the oligonucleotide.

In further embodiments, the pharmaceutical composition is administered subcutaneously.

In some embodiments, the oligonucleotide is in the form of a sodium salt. In some embodiments, the pharmaceutical carrier is WFI (water for injection) and the pharmaceutical composition is adjusted to pH 7.2-7.6.

In other embodiments, the oligonucleotide is in the form of a potassium salt. In some embodiment, where the oligonucleotide is in the form of a potassium salt, the pharmaceutical carrier is WFI and the pharmaceutical composition is adjusted to pH 7.4.

In some embodiments, the form of multiple sclerosis is a relapsing form of multiple sclerosis. In some embodiments is relapsing remitting multiple sclerosis (RRMS).

In other embodiments, the form of multiple sclerosis is a progressive form.

In some embodiments, the pharmaceutical composition is administered as a monotherapy. In other embodiments, the pharmaceutical composition is administered simultaneously or sequentially with at least one additional therapeutic agent.

In some embodiments, where at least one additional therapeutic agent is to be administered, the at least one additional therapeutic agent is a corticosteroid, interferon beta-1a, interferon beta-1b, glatiramer acetate, or ibudilast.

In some embodiments, the active brain lesions are new active brain lesions. In some embodiments, the active brain lesions are GdT1 lesions.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

DETAILED DESCRIPTION OF THE INVENTION

As used herein, an "additional therapeutic agent" is any agent useful for treating multiple sclerosis other than OLIGONUCLEOTIDE 1 having the structure:

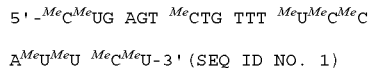

A$^{Me}$U$^{Me}$U $^{Me}$C$^{Me}$U-3' (SEQ ID NO. 1)

wherein
each of the 19 internucleotide linkages of the oligonucleotide is an 0,O-linked phosphorothioate diester;
the nucleotides at the positions 1 to 3 from the 5' end are 2'-O-(2-methoxyethyl) modified ribonucleosides;
the nucleotides at the positions 4 to 12 from the 5' end are 2'-deoxyribonucleosides;
the nucleotides at the positions 13 to 20 from the 5' end are 2'-O-(2-methoxyethyl) modified ribonucleosides; and
all cytosines are 5-methylcytosines ($^{Me}$C).

Within any range listed in this document, all integers and tenths, including integer percentages for percentages, are contemplated as embodiments of this invention. For example, the invention provides that the amount effective to inhibit the conversion of active brain lesions in the human subject may be 50-400 mg; by this recitation the invention contemplates and discloses all tenths and integer mg amounts such as 51.1, 51.2 . . . 399.8, 399.9; 51, 52 . . . 398, 399 mg as embodiments of this invention. Similarly, by another example, the invention provides that the number of active brain lesions detectable by MRI image is lower by 25-80% than the number of active brain lesions detectable by MRI image in a human subject afflicted with the same form of multiple sclerosis not treated with the pharmaceutical composition; by this recitation the invention contemplates and discloses all integer % amounts such as 26%, 27%, 28%, 78% and 79% as embodiments of this invention. Analogously, for every range disclosed in this application.

A pharmaceutically acceptable salt as used herein refers to any salt or stereoisomer form of the oligonucleotide disclosed herein which is appropriate to administer to a human subject. In particular, a potassium salt or a sodium salt as exemplified herein can be used.

Definitions

Kurtzke Expanded Disability Status Scale (EDSS):
The Kurtzke Expanded Disability Status Scale (EDSS) is a method of quantifying disability in multiple sclerosis. The EDSS replaced the previous Disability Status Scales which used to bunch people with MS in the lower brackets. The EDSS quantifies disability in eight Functional Systems (FS) and allows neurologists to assign a Functional System Score (FSS) in each of these. The Functional Systems are: pyramidal, cerebellar, brainstem, sensory, bowel and bladder, visual and cerebral (available on the web at the website: http://www.mult-sclerosis.org/expandeddisabilitystatusscale.html).

Multiple Sclerosis Functional Composite (MSFC):
Multiple Sclerosis Functional Composite (MSFC) is a three-part, standardized, quantitative, assessment instrument for use in clinical studies, particularly clinical trials, of MS (Gary et al., 1999). The MSFC was designed to fulfill three criteria: multidimensional to reflect the varied clinical expression of MS across patients and over time, the dimensions should change relatively independently over time, and one component should be a measure of cognitive function. The three components of the MSFC measure leg function/ambulation, arm/hand function, and cognitive function. MSFC measures disability in MS patients; and used in evaluating the efficacy of experimental or new treatment regimens. MSFC consists of various elements designed to measure arm, leg, and cognitive disability and includes a timed 25-foot walk to measure leg mobility, a nine-hole peg test to measure arm function, and a paced auditory serial addition test to measure cognitive function (available on the website: https://www.nationalmssociety.org/NationalMSSociety/media/MSNationalFiles/Brochures/10-2-3-31-MSFC-_Manual_and_Forms.pdf)

Image Contrast on MRI:
Time constants are involved in relaxation processes that establish equilibrium following radio frequency excitation. As the high-energy nuclei relax and realign they emit energy at rates which are recorded to provide information about the material they are in. The realignment of nuclear spins with the magnetic field is termed longitudinal relaxation and the time required for a certain percentage of the tissue's nuclei to realign is termed "Time 1" or T1 (Spin-lattice relaxation time), which is typically about 1 second at 1.5 tesla main field strength. T2-weighted imaging relies upon local dephasing of spins following the application of the transverse energy pulse; the transverse relaxation time is termed "Time 2" or T2 (spin-spin relaxation time), typically <100 ms for tissue at 1.5 tesla main field strength.

Image contrast is created by using a selection of image acquisition parameters that weights signal by T1 or T2. In the brain, T1-weighting causes the nerve connections of white matter to appear white, and the congregations of neurons of gray matter to appear gray, while cerebrospinal fluid appears dark. The contrast of "white matter," "gray matter" and "cerebrospinal fluid" is reversed using T2 imaging.

As used herein, the term MRI refers to conventional or non-conventional MRI.

Gd-Enhancing Lesions:

The term "Gd-enhancing lesions" refers to lesions that result from a breakdown of the blood brain barrier, which appear in contrast studies using gadolinium contrast agents. Gadolinium enhancement provides information as to the age of a lesion, as Gd-enhancing lesions typically occur within a six week period of lesion formation.

The term "new lesion" includes GdT1 or enlarging T2 lesions not present at a baseline timepoint MRI assessment, but detected in the subject in a subsequent MRI assessment.

T1-Weighted MRI Image:

The term "T1-weighted MRI image" refers to an MR-image that emphasizes T1 contrast by which lesions may be visualized. Abnormal areas in a T1-MRI weighted image are "hypointense" and appear as dark spots. These spots are generally older lesions.

T2-Weighted MRI Image:

The term "T2-weighted MRI image" refers to an MR-image that emphasizes T2 contrast by which lesions may be visualized. T2 lesions represent new inflammatory activity. T2 hyperintensity reflect a range of pathological changes from acute inflammation to irreversible axonal loss.

New Active Lesions

As used herein, "new active lesions" are gadolinium-enhancing or new non-enhancing T2 and/or enlarged non-enhancing T2 lesions.

T1 Black Holes

As used herein, "T1 black holes" are hypointense lesions commonly seen on T1WI in patients with multiple sclerosis. The T1 hyperintense lesions are areas of relatively severe and/or permanent central nervous system (CNS) damage compared with the more non-specific T2-hyperintense lesions, which show greater signal intensity than normal brain on T2-weighted magnetic resonance imaging (MRI). The T1 hyperintense lesions are areas of axonal loss, as well as matrix disruption. T1-hypointense lesions are moderately correlated with focal reduction in the magnetization transfer index and reduced N-acetylaspartate (NAA). There is a correlation between the number of black holes and patient outcomes.

Relapses:

Relapses are characterized by the occurrence of neurological dysfunction symptoms, appearing after a 30-day period of stability or improvement and lasting for more than 24 hours (no infection, no fever). The number of relapses is analyzed using a logistic regression model controlling for treatment and age.

"Relapse Rate" is the number of confirmed relapses per unit time. "Annualized relapse rate" is the mean value of the number of confirmed relapses per each patient multiplied by 365 and divided by the number of days on study drug per each patient.

Progression of Disability:

Progression of disability is assessed by means of valid, sensitive and reliable scales such as EDSS and MSFC. Progression of disability is measured as the achievement of a specified degree of disability or of a sustained worsening of relevant magnitude (1 point when EDSS scores 5.5; 0.5 points if baseline score is >5.5). Alternatively, it can be measured as the time to reach progression or the proportion of individuals who have shown progression at pre-specified time. As a supportive parameter, disability can also be expressed by summary measures obtained from serial measures at scheduled visits, indicating the degree of disability experienced by the patient during a period of time, disregarding whether it is in relation to relapses or not.

Inhibition of progression of disability refers to a reduction of disability at a particular assessment time point in a subject suffering from a form of MS characterized by active lesions and treated according to a method disclosed herein relative to a subject suffering from the same form of MS and not receiving the treatment. In some embodiments, inhibition of progression of disability ranges from at least a 10% reduction in the progression of disability to about a 75% reduction in the progression of disability, e.g., at least a 15%, a 20%, a 30%, a 40%, a 50%, a 60%, or another percent reduction in the progression of disability from at least 10% to about 75%, as determined using any of the above-referenced endpoints or similar ones known in the art.

Oligonucleotide 1:

OLIGONUCLEOTIDE 1 is a second generation phosphorothioate backbone 2'-MOE-modified chimeric oligonucleotide gap-mer designed to hybridize to the 3'-untranslated region of human Very Late Activation Antigen 4 mRNA (VLA-4 mRNA), also known as CD49d mRNA, which codes for the alpha-4 subunit of VLA-4. VLA-4 is also known as alpha-4 integrin (alpha4 beta1). OLIGONUCLEOTIDE 1 selectively inhibits VLA-4 expression in both primary human cells and in several human cell lines by hybridizing to mRNA encoding CD49, which is the α4 subunit of VLA-4.

OLIGONUCLEOTIDE 1 is the 19-sodium salt of a 3'-5' phosphorothioate oligonucleotide 20-mer also referred as a 3-9-8 MOE gap-mer having a molecular weight of 7230 Daltons, in which the nucleotides at positions 1 to 3 from the 5' end are 2'-O-(2-methoxyethyl) modified ribonucleosides (2'-O-(2-methoxyethyl ribose); the nucleotides at positions 4 to 12 from the 5' end are 2'-deoxyribonucleosides of which all cytosines are 5-methylcytosines; the nucleotides at positions 13 to 20 from the 5' end are 2'-O-(2-methoxyethyl) modified ribonucleosides.

```
The sequence of OLIGONUCLEOTIDE 1
(SEQ ID: 1) is:
5'-MeCMeUG AGT MeCTG TTT MeUMeCMeC AMeUMeU MeCMeU-3'
```

The empirical formula of OLIGONUCLEOTIDE 1 is: C233H321N60O129P19S19Na19.

OLIGONUCLEOTIDE 1 may be synthesized by a multi-step process that may be divided into two distinct operations: solid-phase synthesis and downstream processing. In the first operation, the nucleotide sequence of OLIGONUCLEOTIDE 1 is assembled through a computer-controlled solid-phase synthesizer. Subsequent downstream processing includes deprotection steps, preparative reversed-phase (RP) chromatographic purification, isolation and drying to yield OLIGONUCLEOTIDE 1 drug substance. The chemical synthesis of OLIGONUCLEOTIDE 1 utilizes phosphoramidite coupling chemistry followed by oxidative sulfurization and involves sequential coupling of activated monomers to an elongating oligomer, the 3'-terminus of which is covalently attached to the solid support.

Detritylation (Reaction a)

Each cycle of the solid-phase synthesis commences with removal of the acid-labile 5'-O-4,4'-dimethoxytrityl (DMT) protecting group of the 5' terminal nucleoside of the support bound oligonucleotide. This is accomplished by treatment with an acid solution (e.g., dichloroacetic acid (DCA) in toluene). Following detritylation, excess reagent is removed from the support by washing with acetonitrile in preparation for the next reaction.

Coupling (Reaction b)

Chain elongation is achieved by reaction of the 5'-hydroxyl group of the support-bound oligonucleotide with a solution of the phosphoramidite corresponding to that particular base position (e.g., for B2: MOE-Mee amidite) in the presence of an activator (e.g., 1H-tetrazole). This results in the formation of a phosphite triester linkage between the incoming nucleotide synthon and the support-bound oligonucleotide chain. After the coupling reaction, excess reagent is removed from the support by washing with acetonitrile in preparation for the next reaction.

Sulfurization (Reaction c)

The newly formed phosphite triester linkage is converted to the corresponding (0, 0, 0)-trialkyl phosphorothioate triester by treatment with a solution of a sulfur transfer reagent (e.g., phenylacetyl disulfide). Following sulfurization, excess reagent is removed from the support by washing with acetonitrile in preparation for the next reaction.

Capping (Reaction d)

A small proportion of the 5'-hydroxy groups available in any given cycle fail to extend. Coupling of these groups in any of the subsequent cycles would result in formation of process-related impurities ('DMT-on (n−1)-mers') which are difficult to separate from the desired product. To prevent formation of these impurities and to facilitate purification, a 'capping reagent' (e.g., acetic anhydride and N-methylimidazole/acetonitrile/pyridine) is introduced into the reactor vessel to give capped sequences. The resulting failure sequences ('DMT-off shortmers') are separated from the desired product by reversed phase HPLC purification. After the capping reaction excess reagent is removed from the support by washing with acetonitrile in preparation of the next reaction.

Reiteration of this basic four-step cycle using the appropriate nucleoside phosphoramidite allows assembly of the entire protected OLIGONUCLEOTIDE 1 sequence.

Backbone Deprotection (Reaction e)

Following completion of the assembly portion of the process the cyanoethyl groups protecting the (0,0,0)-trialkyl phosphorothioate triester internucleotide linkages are removed by treatment with a solution of triethylamine (TEA) in acetonitrile. The reagent and acrylonitrile generated during this step are removed by washing the column with acetonitrile.

Cleavage from Support and Base Deprotection (Reaction f)

Deprotection of the exocyclic amino groups and cleavage of the crude product from the support is achieved by incubation with aqueous ammonium hydroxide (reaction f). Purification of the crude, 5'-0-DMT-protected product is accomplished by reversed-phase high pressure liquid chromatography (RP-HPLC). The RP-HPLC step removes DMT-off failure sequences. The elution profile is monitored by UV absorption spectroscopy. Fractions containing DMT-on OLIGONUCLEOTIDE 1 product are collected and analyzed.

Acidic Deprotection (Reaction g)

RP-HPLC fractions containing 5'-0-DMT-protected OLIGONUCLEOTIDE 1 are pooled and transferred to precipitation tank. The products obtained from the purification of several syntheses are combined at this stage of the process. Purified DMT-on OLIGONUCLEOTIDE 1 is treated with acid (e.g., acetic acid) to remove the DMT group attached to the 5' terminus. After acid exposure for the prescribed time and neutralization, OLIGONUCLEOTIDE 1 drug substance is isolated and dried.

Following the final acidic deprotection step (reaction g), the solution is neutralized by addition of aqueous sodium hydroxide and OLIGONUCLEOTIDE 1 drug substance is precipitated from solution by adding ethanol. The precipitated material is allowed to settle at the bottom of the reaction vessel and the ethanolic supernatant decanted. The precipitated material is redissolved in purified water and the solution pH adjusted to between pH 7.2 and 7.3. The precipitation step is repeated. The precipitated material is dissolved in water and the solution filtered through a 0.45 micron filter and transferred into disposable polypropylene trays that are then loaded into a lyophilizer. The solution is cooled to −50° C. Primary drying is carried out at 25° C. for 37 h. The temperature is increased to 30° C. and a secondary drying step performed for 5.5 h. Following completion of the lyophilization process, the drug substance is transferred to high density polyethylene bottles and stored at −20° C.

Forms of Multiple Sclerosis:

There are five distinct disease stages and/or types of MS:
1) benign multiple sclerosis;
2) relapsing-remitting multiple sclerosis (RRMS);
3) secondary progressive multiple sclerosis (SPMS);
4) progressive relapsing multiple sclerosis (PRMS; and
5) primary progressive multiple sclerosis (PPMS).

Benign multiple sclerosis is a retrospective diagnosis which is characterized by 1-2 exacerbations with complete recovery, no lasting disability and no disease progression for 10-15 years after the initial onset. Benign multiple sclerosis may, however, progress into other forms of multiple sclerosis.

Patients suffering from RRMS experience sporadic exacerbations or relapses, as well as periods of remission. Lesions and evidence of axonal loss may or may not be visible on MRI for patients with RRMS.

SPMS may evolve from RRMS. Patients afflicted with SPMS have relapses, a diminishing degree of recovery during remissions, less frequent remissions and more pronounced neurological deficits than RRMS patients Enlarged ventricles, which are markers for atrophy of the corpus callosum, midline center and spinal cord, are visible on MRI of patients with SPMS.

PPMS is characterized by a steady progression of increasing neurological deficits without distinct attacks or remissions. Cerebral lesions, diffuse spinal cord damage and evidence of axonal loss are evident on the MRI of patients with PPMS. PPMS has periods of acute exacerbations while proceeding along a course of increasing neurological deficits without remissions. Lesions are evident on MRI of patients suffering from PRMS (Johnson et al., 1986).

A clinically isolated syndrome (CIS) is a single monosymptomatic attack compatible with MS, such as optic neuritis, brain stem symptoms, and partial myelitis. Patients with CIS that experience a second clinical attack are generally considered to have clinically definite multiple sclerosis (CDMS). Over 80 percent of patients with a CIS and MRI lesions go on to develop MS, while approximately 20 percent have a self-limited process (Brex et al., 2002; Frohman et al., 2003).

Multiple sclerosis may present with optic neuritis, blurring of vision, diplopia, involuntary rapid eye movement, blindness, loss of balance, tremors, ataxia, vertigo, clumsiness of a limb, lack of co-ordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning.

Relapsing Form of Multiple Sclerosis:
The term relapsing MS includes:
1) patients with RRMS;
2) patients with SPMS and superimposed relapses; and
3) patients with CIS who show lesion dissemination on subsequent MRI scans according to McDonald's criteria.

As used herein, relapsing forms of multiple sclerosis include:
Relapsing-remitting multiple sclerosis (RRMS), characterized by unpredictable acute episodes of neurological dysfunction (relapses), followed by variable recovery and periods of clinical stability;
Secondary progressive MS (SPMS), wherein patients having RRMS develop sustained deterioration with or without relapses superimposed; and
Primary progressive-relapsing multiple sclerosis (PPRMS) or progressive-relapsing multiple sclerosis (PRMS), an uncommon form wherein patients developing a progressive deterioration from the beginning can also develop relapses later on.

As used herein, "course of administration" refers to the entire treatment from the first administration of the compound and continuing until any cessation of periodic administration. For example, the compound may be administered once every month for 2 months, or for 6 months, or for 12 months, or for 2 years, etc.

EXAMPLES

OLIGONUCLEOTIDE 1 can be obtained by the process disclosed in U.S. Pat. Nos. 5,968,826, 6,242,591 and 6,258,790, the contents of which are hereby incorporated by reference. OLIGONUCLEOTIDE 1, also known as ATL1102, has been tested in a multicenter, double-blind, placebo-controlled randomized phase II trial, in 77 patients with RRMS, and the new active MRI lesion and GdT2 lesion efficacy and safety outcomes are published in the scientific literature by Limmroth et al., 2014.

The efficacy and safety of a selected treatment regimen of OLIGONUCLEOTIDE 1 using MRI in patients with RRMS compared to placebo is also disclosed in U.S. Pat. Nos. 8,415,314 and 8,759,314, the contents of which are hereby incorporated by reference. Example 1 of U.S. Pat. Nos. 8,415,314 and 8,759,314, outlines the treatment methods, including patient exclusion criteria, patient populations, dosing regimen (1 week induction cycle, 7 week maintenance cycle), and 8 week off-treatment cycle, drug product, measurements, urine and blood samples, pharmacokinetics, and results of the primary outcome measure (reduction in the cumulative week 4, 8 and 12 number of new active MS lesions (either new Gd T1 lesions or nonenhancing new or enlarging T2 lesions) and secondary outcome measures (reduction in cumulative week 4, 8 and 12 number of GdT1 lesions), and additional measures of thrombocytopenia safety and pharmacokinetic data.

The new efficacy data with regard to the significant reduction in active and new active MS lesions converting to black holes is provided below in Example 1.

Example 1

To Evaluate the Efficacy of a Selected Treatment Regimen of OLIGONUCLEOTIDE 1 ATL1102, in Reducing the Proportion of New Active Brain Lesions Converting to Hypointense T1-Weighted Lesions in Patients with Relapsing Remitting MS (RRMS) Compared to Placebo.

Background

In a multicenter, double-blind, placebo-controlled randomized phase II trial, 77 patients with RRMS were treated with 200 mg of ATL1102 subcutaneously injected 3 times in the first week and twice weekly for 7 weeks or placebo and monitored for a further 8 weeks. MRI scans were taken at baseline and weeks 4, 8, 12, and 16. The primary endpoint in Phase II was the cumulative number of new active lesions (either new gadolinium-enhancing T1 lesions or nonenhancing new or enlarging T2 lesions) at weeks 4, 8, and 12 in treated vs placebo. In the Phase II study ATL1102 dosed for 8 weeks in RRMS patients met its primary endpoint in reducing the cumulative number of new active MS lesions by 54% vs placebo at 12 weeks (P=0.01) (Limmroth et al., 2014). Notably, ATL1102 treated patients had 90% fewer new GdT1 lesions than those receiving placebo at 12 weeks (P<0.005).

MRI

Five MRI scans were performed per patient, to be taken for baseline setting (Day −7), at week 4 (after 9 doses), week 8 (after 17 doses), week 12, and week 16. An additional MRI scan was performed in case of relapse. MRI assessment was done by:
T2-weighted images;
Precontrast T1-weighted images; and
Post-gadolinium T1-weighted images.

MRI scans were analyzed by the IAC (Image Analysis Centre, VU Medical Centre, Amsterdam, The Netherlands) by an experienced reader blinded to treatment allocation.

Prior to initiation, each centre had asked to send a dummy scan to assess image quality and shipment procedures, and to evaluate the accessibility of the electronic data carrier. This was used to fine-tune the exact MRI sequences, which were vendor-specific. Only upon final approval of the dummy scan were the sites allowed to start scanning patients, with no deviations from the final scan-protocol for that particular site being allowed. Once patients had been enrolled, for each scan performed, the quality was assessed at the IAC and was reported to the contributing site, as part of an ongoing Quality Assurance procedure. Once the data had arrived at the IAC they were logged, copied and stored. Both sites and monitors were duly informed by fax about acceptance of scans. Lesions were marked on the hard copies by a radiologist blinded to full patient identification and treatment allocation.

MRI Image Acquisition

The patient's position had been standardized by putting the patient's head into the head coil in a well-defined fashion (e.g. nasal bridge at the centre). Rotation in the coronal plane was minimized by centering a horizontal light beam at the centre of the coil as well as across the orbital ridge. The head of the patient had been supported within the head-coil with foam cushions in order to minimize patient motion. Rotation in the horizontal plane had been minimized by centering a vertical light beam on the nose. A long IV line connected to a drip infusion with saline had been inserted prior to moving the patient into the scanner so that gadolinium could be injected during the session without moving the table (thus avoiding movement of the patients head between sequences).

All MR sequences were performed using 3 mm thick slices, with a 25 cm field of view (FOV), and a 256×256 square matrix to produce roughly 1 by 1 mm pixels. The actual scanning started with sagittal T1-weighted spin-echo (SE) localizer images. All transaxial images were planned from the mid-sagittal image, using 2×23 interleaved sections with a thickness of 3 mm using a 3 mm (100%) gap. This resulted in 46 consecutive slices with a z-range of 13.8 cm, thus covering the head from vertex to foramen magnum; the middle slice of the upper series was aligned with the inferior border of the splenium of the corpus callosum.

A rectangular (e.g., ¾ or 75%) FOV was used. It allowed a propor ional reduction in the number of phase encoding steps (e.g., 192 instead of 256), as long as 1×1 mm square pixels were obtained without unfolding artefacts (right to left phase encoding for the transaxial images). Techniques such as "half-Fourier transform", "reduced scan-percentage" (Philips Healthcare; Best, The Netherlands) or "½ NEX" (General Electric Healthcare; Tirat Hacarmel, Israel) were not employed, as they substantially reduce the signal-to-noise ratio.

The first transaxial sequence (following the pilot scans), was a pre-contrast T1-weighted conventional spin-echo (SE) [TR 400-700 ms/TE 5-25 ms/2 excitations]. Afterwards, gadolinium-DTPA was administered at a standard dose of 0.1 mmol/kg, via the long IV line. The second transaxial series was a dual echo SE [2000-3000 ms/TE1: 15-40 ms, TE2: 60-100 ms/1 excitation]. When a turbo- or fast-SE was used the turbo-factor was limited (e.g., 5-6). The third and final transaxial sequence was a post-contrast T1-weighted conventional SE [400-700 ms/5-25 ms/2 excitations].

Methods to Assess Effects on the Evolution on Remaining (New) Active Lesions into Black Holes analysis on at least the Screening, Week 4, Week 8 or Week 12 visit. The MRI protocol included T2-weighted images and T1-weighted images before and after standard dose gadolinium for all time points.

Black Hole Evolution Analysis by IAC

The BH evolution of all active lesions as originally assessed in the ATL1102 study were analyzed for this post hoc study. New active lesions were defined as new T1 gadolinium lesions, new (non-enhancing) T2 lesions or enlarged (non-enhancing) T2 lesions. Additionally T1 gadolinium lesions on screening were considered active lesions.

T2 lesions on screening were considered to be non-active (persisting). Active lesions on the last visit, Week 16, were not included, since it was not possible to establish whether the accompanying black holes were acute or persisting without a follow up visit.

One reviewer, blinded to treatment arms, used the T1-weighted images before contrast to detect black holes on the location of the (new) active lesions on the visit of origin as well as on the following visits.

41 eligible patients received placebo, in a similar manner as OLIGONUCLEOTIDE 1. 77 patients had completed the study.

Results

TABLE 1

Results of Logistic Regression Week 8-12

| Analysis Black Hole Evolution | Characteristics | Placebo (arm1) | ATL1102 (arm2) |
|---|---|---|---|
| Origin active lesions week 8-12 combined | N = number of patients | 23 | 17 |
|  | Active lesions, mean (SD) | 7.1 (7.9) | 3.1 (3.4) |
|  | Active lesions, median (range) | 4 (1-33) | 2 (1-13) |
|  | % BH Conversions[1], | 45/163 = 27.6% | 7/53 = 13.3% |
|  | Overall Ratio[2], mean (SD) | 23.6 (32.0) | 19.2 (38.8) |
| Treatment Arm Comparison | P-value = 0.0376 |  |  |
|  | Odds Ratio: Arm 1 v Arm 2:2.506, 95% CI, (1.054, 5.959) |  |  |
|  | There is a significant difference between Placebo and ATL1102 |  |  |

Notes:
[1] % BH Conversion is the sum of converted/sum of active in each arm, no standard deviations are derived for this measure.
[2] Overall Ratio = The average of individual Converted lesions/Active lesions in each arm.

A post hoc analysis of the MRI data was conducted by the Image Analysis Center (IAC) VU Medical Center, Amsterdam, The Netherlands, to measure the effect of ATL1102 on the conversion of (new) active lesions to T1 black holes (BH). BH represents areas of axonal loss and permanent tissue damage. In the Phase II study, new active lesions were defined as either GdT1 or new-enlarging T2 not present at baseline.

From the original ATL1102 dataset, the IAC determined 51 subjects had lesion activity suitable for black hole Black Hole Evolution Analysis Week 8 to Week 12

ATL1102 significantly reduced the (mean) number of week 8 and 12 active lesions converting to BH at week 16 to 13.3% compared to 27.6% in placebo.

The blackhole data were analysed with a logistic regression of treatment groups with a binomial error distribution (Zivadinov et al., 2015). The odds of converting in the placebo arm were 2.51 (with 95% Wald Confidence Interval: (1.054, 5.959) and p-value=0.0376) times the odds of converting in the treatment arm.

TABLE 2

Results of Logistic Regression Week 4 to Week 8

| Analysis Black Hole Evolution | Characteristics | Placebo (arm1) | ATL1102 (arm2) |
|---|---|---|---|
| Origin active lesions week | N = number of patients | 24 | 19 |
|  | Active lesions, mean (SD) | 6.0 (5.9) | 4.7 (7.5) |

TABLE 2-continued

| Analysis Black Hole Evolution | Characteristics | Placebo (arm1) | ATL1102 (arm2) |
|---|---|---|---|
| Results of Logistic Regression Week 4 to Week 8 | | | |
| 4-8 combined | Active lesions, median (range) | 3.5 (1-26) | 1.0 (1-32) |
| | % BH Conversions: | 31/144 = 21.5% | 18/89 = 20.2% |
| | Overall Ratio, mean (SD) | 16.7 (26.5) | 23.2 (32.3) |
| Treatment Arm Comparison | P-value = 0.8126 | | |
| | Odds Ratio: Arm 1 v Arm 2:1.082, 95% CI, (0.564, 2.077) | | |
| | No significant differences between Placebo and ATL1102 | | |

Notes:
[1] % BH Conversion is the sum of converted/sum of active in each arm, no standard deviations are derived for this measure.
[2] Overall Ratio = The average of individual Converted lesions/Active lesions in each arm.

Black Hole Evolution Analysis Week 4 to Week 8

No significant difference in BH evolution was observed between ATL1102 treated and placebo in the (mean) number of active lesions found at week 4 to week 8, converting to BH by week 16. The mean number of active lesions converting to BH by week 16 was 21.5% for ATL1102, compared to 20.2% in placebo.

The blackhole data were analysed with a logistic regression of treatment groups with a binomial error distribution (Zivadinov et al., 2015). There was no significant difference in BH evolution between ATL1102 and placebo in the week 4 to week 8 group by week 16 with p-value 0.8126.

TABLE 3

| Analysis Black Hole Evolution | Characteristics | Placebo (arm1) | ATL1102 (arm2) |
|---|---|---|---|
| Results of Logistic Regression Screening to Week 4 | | | |
| Origin active lesions screening-week 4 combined | N = number of patients | 22 | 19 |
| | Active lesions, mean (SD) | 5.3 (5.5) | 4.8 (7.3) |
| | Active lesions, median (range) | 3 (1-21) | 2 (1-29) |
| | % BH Conversions | 28/127 = 24.4% | 23/92 = 25% |
| | Overall Ratio, mean (SD) | 20.3 (32.3) | 23.56 (34.7) |
| Treatment Arm Comparison | P-value = 0.8583 | | |
| | Odds Ratio: Arm 1 v Arm 2, 0.944, 95% CI, (0.500, 1.781) | | |
| | No significant differences between Placebo and ATL1102 | | |

Notes:
[1] % BH Conversion is the sum of converted/sum of active in each arm, no standard deviations are derived for this measure.
[2] Overall Ratio = The average of individual Converted lesions/Active lesions in each arm.

Black Hole Evolution Analysis Screening to Week 4

No significant difference in BH evolution was observed between ATL1102 treated and placebo in the (mean) number of active lesions found at screening and 4 weeks, converting to BH by week 16. The mean number of screening and week 4 active lesions converting to BH by week 16 was 24.4% for ATL1102, compared to 25% in placebo.

The blackhole data were analysed with a logistic regression of treatment groups with a binomial error distribution (Zivadinov et al., 2015). There was no significant difference in BH evolution between ATL1102 and placebo in the screening to week 4 group by week 16 with p-value 0.8583.

CONCLUSIONS

There was a significant reduction in the number of active lesions converting to BH at week 16 in ATL1102 treated patients (13.3%) compared to in those patients on placebo (27.6%). The blackhole data were analysed with a logistic regression of treatment groups with a binomial error distribution (Zivadinov et al., 2015) as required. The odds of converting to a BH in the placebo arm were 2.51 (p=0.0376) times the odds of converting in the treatment arm.

The ATL1102 group had less active lesions converting to black holes then the placebo group.

There were no significant differences in BH evolution observed between ATL1102 treated and placebo in the (mean) number of active lesions found at screening and 4 weeks, and weeks 4 and weeks 8, converting to BH by week 16.

OLIGONUCLEOTIDE 1, in a placebo controlled, double-blind trial in RRMS patients, was shown to be effective in preventing accumulation of new active lesions detectable by MRI in the brain and slowing the proportion of active lesions that convert to black hole.

REFERENCES

McDonald et al., Recommended Diagnostic Criteria for Multiple Sclerosis: Guidelines from the International Panel on the Diagnosis of Multiple Sclerosis, Ann Neurol (2001) 50:121-127.

CPMP Committee for Proprietary Medicinal Products, Note for Guidance on Good Clinical Practice, London, 1997, January; CPMP/ICH/135/95:1-58.

CPMP Committee for Proprietary Medicinal Products, Note for Guidance on Clinical Investigation of Medicinal Products for the Treatment of Multiple Sclerosis, London, 1999, July 28; CPMP/EWP/561/98:1-10.

Alonso and Mernan, Temporal trends in the incidence of multiple sclerosis: a systematic review, Neurology (2008) 71(2) 129-35.

Johnson et al., Cell-mediated immunity to myelin-associated glycoprotein, proteolipid protein, and myelin basic protein in multiple sclerosis, J. Neuroimmunol. (1986) 13(1): 99-108.

Chou et al., Frequency of T cells specific for myelin basic protein and myelin proteolipid protein in blood and cerebrospinal fluid in multiple sclerosis, J, Neuroimmunol. (1992) 38(1-2):105-13.

de Rosbo et al., Reactivity to myelin antigens in multiple sclerosis. Peripheral blood lymphocytes respond predominantly to myelin oligodendrocyte glycoprotein, J. Clin. Invest. (1993) 92(6):2602-8.

de Rosbo and Ben-Nun A, T-cell responses to myelin antigens in multiple sclerosis; relevance of the predominant autoimmune reactivity to myelin oligodendrocyte glycoprotein, J. Autoimmun. (1998) 11(4):287-99.

van Noort et al., The small heat-shock protein alpha B-crystallin as candidate autoantigen in multiple sclerosis, Nature (1995) 29:375(6534):798-801.

Pelfrey et al., T cell response to two immunodominant proteolipid protein (PLP) peptides in multiple sclerosis patients and healthy controls, Mult. Scler. (1996) 1(5): 270-8.

Diaz-Villoslada et al., "Autoreactivity to myelin antigens: myelin/oligodendrocyte glycoprotein is a prevalent autoantigen", J. Neuroimmunol., (1999) 99(1):36-43.

Pender et al., Surges of increased T cell reactivity to an encephalitogenic region of myelin proteolipid protein occur more often in patients with multiple sclerosis than in healthy subjects, J. Immunol. (2000) 165(9):5322-31.

Rovira and Leo, MR in the diagnosis and monitoring of multiple sclerosis: An overview, Eur J Radiol (2008) 67(3):409-14.

Van Oosten et al., Treatment of multiple sclerosis with the monoclonal anti-CD4 antibody cM-T412: results of a randomised, double-blind, placebo-controlled MR-monitored phase II trial, Neurology (1997) 49:351-357.

Polman et al., AFFIRM Investigators. A randomized, placebo-controlled trial of natalizumab for relapsing multiple sclerosis, N. Engl. J. Med. (2006) 354:899-910.

Coles et al., CARE-MS II investigators. Alemtuzumab for patients with relapsing multiple sclerosis after disease-modifying therapy: a randomised controlled phase 3 trial, Lancet (2012) 380 (9856):1829-39.

Hauser et al., OPERA I and OPERA II Clinical Investigators. Ocrelizumab versus Interferon Beta-1a in Relapsing Multiple Sclerosis, N. Engl J. Med (2017) 376 (3): 221-234.

Plavina, et al., Anti-JC virus antibody levels in serum or plasma further define risk of natalizumab-associated progressive multifocal leukoencephalopathy. Ann Neurol, (2014) 76:802-12.

Havla et al., Interdisciplinary Risk Management in the Treatment of Multiple Sclerosis, Dtsch Arztebl Int. (2016) 113(51-52):879-886.

Montalban et al., Ocrelizumab versus placebo in primary progressive multiple sclerosis, N. Engl J. Med (2017) 376; 209-220.

Stankiewicz et al., Neurotherapeutics (2013) 10:77-88.

Kappos et al., Efficacy and safety of siponimod in secondary progressive MS: Results of the placebo controlled, double-blind, Phase III EXPAND study, ECTRIMS (2016) Abstract 250.

Barkhof et al., Neurology (2010) 74:1033-1040.

Brex et al., Neurology (2001) 57: 2185-2190.

Kuang-Yu et al., Suppression of Gene Expression by Targeted Disruption of Messenger RNA, Stem Cells (2000) 18:307-319.

Helene and Toulme, Specific regulation of gene expression by antisense, sense and antigene nucleic acids, Biochim. Biophys. Acta (1990) 1049(2):99-125.

Cohen, Antisense oligodeoxynucleotides as antiviral agents, Antiviral. Res., (1991) 16(2):121-33.

Calabretta, Inhibition of protooncogene expression by antisense oligodeoxynucleotides: biological and therapeutic implications, Cancer Res. (1991) 51(17):4505-10.

Crooke, Progress toward oligonucleotide therapeutics: pharmacodynamics properties, Faseb J. (1993) 7(6): 533-9.

Crooke, Therapeutic Applications of oligonucleotide, Annual Review Pharmacol. Toxicol (1992) 32:329-76.

Hemler et al., Characterization of the cell surface heterodimer VLA-4 and related peptides, J. Biol Chem (1987) 262(24):11478-85.

Tchilian et al., Anti-alpha 4 integrin antibody induces apoptosis in murine thymocytes and staphylococcal enterotoxin B-activated lymph node T-cells, Immunology (1997) 92:321-327.

Lo et al., Integrin-dependence of lymphocyte entry into the splenic white pulp, J. Exp. Med. (2003) 197(3):353-361.

Alter et al., Determinants of human B-cell migration across brain endothelial cells. J. Immunol. (2003) 170(9):4497-4505.

Niino et al., Natalizumab effects on immune cell responses in multiple sclerosis, Ann. Neurol. (2006) 59 (6):748-754.

Carrasco and Batista, B-cell activation by membrane-bound antigens is facilitated by the interaction of VLA-4 with VCAM-1, EMBO (2006) 25:889-899.

Steinman, Blocking adhesion molecules as therapy for multiple sclerosis: natalizumab, Nature Reviews Drug Discovery (2005) 4:510-518.

Gary R et al., Development of a multiple sclerosis functional composite as a clinical trial outcome measure, Brain (1999) 122:871-882.

Brex et al., A longitudinal study of abnormalities on MRI and isability from multiple sclerosis, N. Engl. J. Med. (2002) 346(3):158-64.

Frohman et al., The utility of MRI in suspected MS: report of the Therapeutics and Technology Assessment Subcommittee of the American Academy of Neurology, Neurology (2003) 61(5):602-11.

Limmroth, et al., CD49d antisense drug ATL1102 reduces disease activity in patients with relapsing-remitting MS, Neurology (2014) 83(20):1780-1788.

Bastianello et al., Changes in magnetic resonance imaging disease measures over 3 years in mildly disabled patients with relapsing-remitting multiple sclerosis receiving interferon b-1a in the COGnitive Impairment in Multiple Sclerosis (COGIMUS) study, BMC Neurology (2011) 11:125.

Zivadinov et al., Effect of glatiramer acetate three-times weekly on the evolution of new, active, multiple sclerosis lesions into T1-hypintense "black holes": a post hoc magnetic resonance imaging analysis, J. Neurol. (2015) 262:648-653.

What is claimed is:

1. A method for treating a human subject afflicted with a form of multiple sclerosis (MS) characterized by the presence of active brain lesions detectable by MRI, the method comprising:
   (i) imaging the subject by MRI or obtaining an MRI image of the subject to detect new active brain lesions;
   (ii) following the imaging, administering to the human subject a pharmaceutical composition comprising a pharmaceutically acceptable carrier and an oligonucleotide corresponding to OLIGONUCLEOTIDE I having the structure:

$$5'-{}^{Me}C{}^{Me}UG\ AGT\ {}^{Me}CTG\ TTT\ {}^{Me}U{}^{Me}C{}^{Me}C$$
   $$A{}^{Me}U{}^{Me}U\ {}^{Me}C{}^{Me}U-3'\ (SEQ\ ID\ NO.\ 1)$$

wherein
   each of the 19 internucleotide linkages of the oligonucleotide is an O,O-linked phosphorothioate diester;
   the nucleotides at the positions 1 to 3 from the 5' end are 2'-O-(2-methoxyethyl) modified ribonucleosides;
   the nucleotides at the positions 4 to 12 from the 5' end are 2'-deoxyribonucleosides;
   the nucleotides at the positions 13 to 20 from the 5' end are 2'-O-(2-methoxyethyl) modified ribonucleosides; and
   all cytosines are 5-methylcytosines ($^{Me}C$);
   or a pharmaceutically acceptable salt of the oligonucleotide; and
   (iii) following the administration, imaging the subject by MRI or obtaining an MRI image of the subject and detecting in the image that the conversion of the detected new active brain lesions from (i) to new hypointense T1-weighted lesions is inhibited,
   whereby the administration of the pharmaceutical composition is in a dose effective to inhibit the conversion of active brain lesions in the subject into hypointense T1-weighted lesions.

2. The method of claim 1, wherein the administration inhibits one or more of percentage brain volume change (PBVC), atrophy, or progression of disability in the human subject.

3. The method of claim 1, wherein the proportion of active brain lesions converted into hypointense T1-weighted lesions detectable by MRI after treatment is at least 10% lower than the proportion of active brain lesions converted into hypointense T1-weighted lesions detectable by MRI in a human subject afflicted with the same form of MS, but not treated with the pharmaceutical composition.

4. The method of claim 1, wherein the proportion of active brain lesions converted into hypointense T1-weighted lesions detectable by MRI is about 13% after 8 weeks of treatment with the pharmaceutical composition.

5. The method of claim 1, wherein the number of active brain lesions detectable by MRI is reduced by 35%-90% relative to the number in a human subject afflicted with the same form of MS, but not treated with the pharmaceutical composition.

6. The method of claim 1, comprising a periodic administration of the pharmaceutical composition:
   (i) three times per week;
   (ii) twice per week; or
   (iii) once per week.

7. The method of claim 1, comprising a periodic administration of the pharmaceutical composition:
   (i) once every two weeks;
   (ii) once every three weeks;
   (iii) once every four weeks;
   (iv) once per month; or
   (v) once per two months.

8. The method of claim 1, wherein the pharmaceutical composition comprises 25-400 mg of the oligonucleotide.

9. The method of claim 8, wherein the pharmaceutical composition comprises:
   (i) 300 mg of the oligonucleotide;
   (ii) 200 mg of the oligonucleotide;
   (iii) 150 mg of the oligonucleotide;
   (iv) 100 mg of the oligonucleotide;
   (v) 70 mg of the oligonucleotide;
   (vi) 50 mg of the oligonucleotide; or
   (vii) 25 mg of the oligonucleotide.

10. The method of claim 1, wherein the pharmaceutical composition is administered:
    (i) as a monotherapy; or
    (ii) simultaneously or sequentially with at least one additional therapeutic agent.

11. The method of claim 10, wherein the at least one additional therapeutic is a corticosteroid, interferon beta-1a, interferon beta-1b, glatiramer acetate, or ibudilast.

12. The method of claim 1, wherein the oligonucleotide is in the form of a sodium salt or a potassium salt.

13. The method of claim 1, wherein the pharmaceutically acceptable carrier is water for injection (WFI) and the pharmaceutical composition is adjusted to pH 7.2-7.6.

14. The method of claim 1, wherein the oligonucleotide is in the form of a stereoisomer.

15. The method of claim 1, wherein the form of multiple sclerosis is a relapsing form of multiple sclerosis or a progressive form of multiple sclerosis.

16. The method of claim 15, wherein the relapsing form of multiple sclerosis is relapsing remitting multiple sclerosis (RRMS).

17. The method of claim 1, wherein the pharmaceutical composition is administered subcutaneously.

18. The method of claim 1, wherein the active brain lesions are new active brain lesions.

19. The method of claim 1, wherein the active brain lesions are GdT1 lesions.

20. The method of claim 1, wherein (iii) is conducted from 8 to 12 weeks following (ii).

21. The method of claim 1, wherein the proportion of active brain lesions converted into hypointense T1-weighted lesions detectable by MRI after treatment is at least 10% lower than the proportion of active brain lesions converted into hypointense T1-weighted lesions detectable by MRI in a human subject afflicted with the same form of MS, but not treated with the pharmaceutical composition, wherein the pharmaceutical composition is administered at least twice per week, and wherein the pharmaceutical composition comprises 200 mg of the oligonucleotide.

* * * * *